United States Patent

Hame et al.

[11] Patent Number: 5,964,485
[45] Date of Patent: *Oct. 12, 1999

[54] TUBE COUPLING

[75] Inventors: David R. Hame, Copthorne; Howard Barratt, Pulborough, both of United Kingdom

[73] Assignee: E.R. Squibb & Sons, Inc., Princeton, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/677,706

[22] Filed: Jul. 10, 1996

[51] Int. Cl.⁶ .................................................. F16L 37/08
[52] U.S. Cl. ........................ 285/320; 285/308; 285/423
[58] Field of Search ................................... 285/319, 320, 285/423, 308

[56] References Cited

U.S. PATENT DOCUMENTS

| | | | |
|---|---|---|---|
| 4,110,144 | 8/1978 | Buehler et al. | 285/423 |
| 4,174,125 | 11/1979 | Wyss | 285/423 |
| 4,537,426 | 8/1985 | Carter, Sr. | 285/423 |
| 4,542,922 | 9/1985 | Grossauer | 285/423 |
| 4,625,998 | 12/1986 | Draudt et al. | 285/423 |
| 4,796,669 | 1/1989 | St. Onge | 285/423 |
| 5,078,429 | 1/1992 | Braut et al. | 285/320 |
| 5,324,082 | 6/1994 | McNaughton | 285/319 |
| 5,466,017 | 11/1995 | Szabo et al. | 285/319 |

FOREIGN PATENT DOCUMENTS

| | | | |
|---|---|---|---|
| 275749 | 7/1988 | European Pat. Off. | 285/423 |
| 2352238 | 12/1977 | France | 285/423 |
| 5-272680 | 10/1993 | Japan | 285/319 |
| 5-280679 | 10/1993 | Japan | 285/319 |
| 2077377 | 12/1981 | United Kingdom | 285/319 |
| 2113788 | 8/1983 | United Kingdom | 285/423 |

*Primary Examiner*—Eric K. Nicholson
*Attorney, Agent, or Firm*—Stuart E. Krieger

[57] ABSTRACT

A tube coupling is shown, particularly but not exclusively intended for use in joining tubes which have medical and surgical uses. A coupling according to the invention may be used to connect an ostomy bag to a drainage tube, or to connect an incontinence urine collection device to a drainage tube, or to connect a drainage tube to a drainage bag, or a catheter to a drainage tube. A tube coupling has a male part and a female part. The former has a radially extending external peripheral rib near its free end. The female part is made in one piece and comprises a tubular shell of a relatively rigid plastics material provided with an annular internal recess. The recess has molded therein a hollow tubular member of a relatively soft plastics material. The female part has no loose parts to become detached, can be made inexpensively by a "two-shot" molding process, and provides extremely good security against leakage.

3 Claims, 2 Drawing Sheets

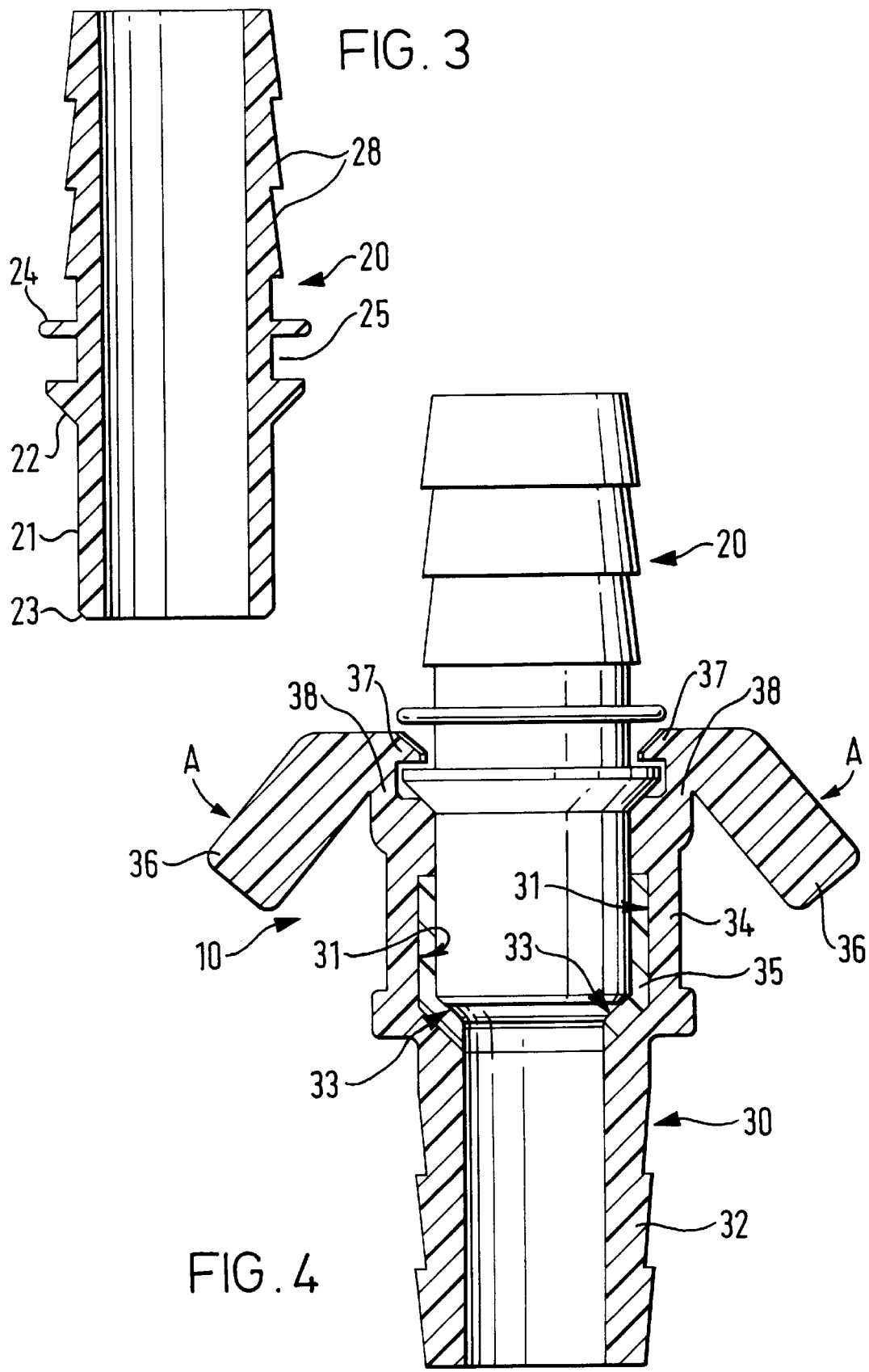

TUBE COUPLING

The present invention relates to a tube coupling, particularly but not exclusively intended for use in joining tubes such as have medical and surgical uses. Such tube couplings are often made wholly of plastics material. A coupling according to the invention may be used to connect an ostomy bag to a drainage tube, or to connect an incontinence urine collection device to a drainage tube, or to connect a drainage tube to a drainage bag, or a catheter to a drainage tube. Other applications will occur to the reader.

Many different designs of tube coupling have been suggested in the prior art, see for example, the proposals of SARNS INC. in British Patent Specification No. 1,193,759 and MANLY in U.S. Pat. Ser. No. 3,245,703. Other proposals can be seen in British Patents Nos. 1,334,486; 1,506,962; 2,091,365 and 2,092,690. In some circumstances, particularly in medical applications, users have found difficulties in manipulating prior designs of coupling. In most prior designs of coupling in medical use, rotation between the coupling parts has been precluded in the interest of maintaining a good liquid seal. This is the case, for example in the coupling shown in FIGS. 10 and 11 of published U.K. Patent Application No. 2,061,466.

According to one aspect of the invention, there is provided a tube coupling comprising a male part and a female part, the former having a radially extending external peripheral rib near the free end of the male part, and the female part being made in one piece and comprising a tubular shell of a relatively rigid plastics material provided with an annular internal recess, the recess having moulded therein a hollow tubular member of a relatively soft plastics material.

The advantages of this arrangement over, for example, that shown in British Patent 2,092,690 are that the female part has no loose parts to become detached, can be made inexpensively by a "two-shot" moulding process, and provides extremely good security against leakage. Such a coupling is particularly effective in handling aggressive liquids such as urine. Fastening hooks are formed integral with the female part and so cannot become detached from the coupling.

According to another aspect of the invention, there is provided a method of making a female part of a tube coupling, which comprises employing a "two-shot" moulding process known per se, an outer tubular portion of the coupling being moulded from a relatively rigid thermoplastics elastomer and a tubular inner cushioning and sealing portion of the female part being moulded from a relatively soft thermoplastics elastomer.

According to a preferred embodiment of the invention, the tubular cushioning and sealing portion of the coupling has a substantially cylindrical internal surface for a major portion of its length and has, at its end furthest from the free end of the female coupling part, an inwardly-tapering portion. This is designed to receive and abut the free end of the male part of the coupling, so further reducing the possibility of leakage.

The invention will be better understood from a consideration of a particular embodiment as shown in the accompanying drawings, in which:

FIG. 3 is an axial cross-section of a male coupling part; and

FIG. 4 shows the male and female parts joined to form a coupling.

Figure 1:
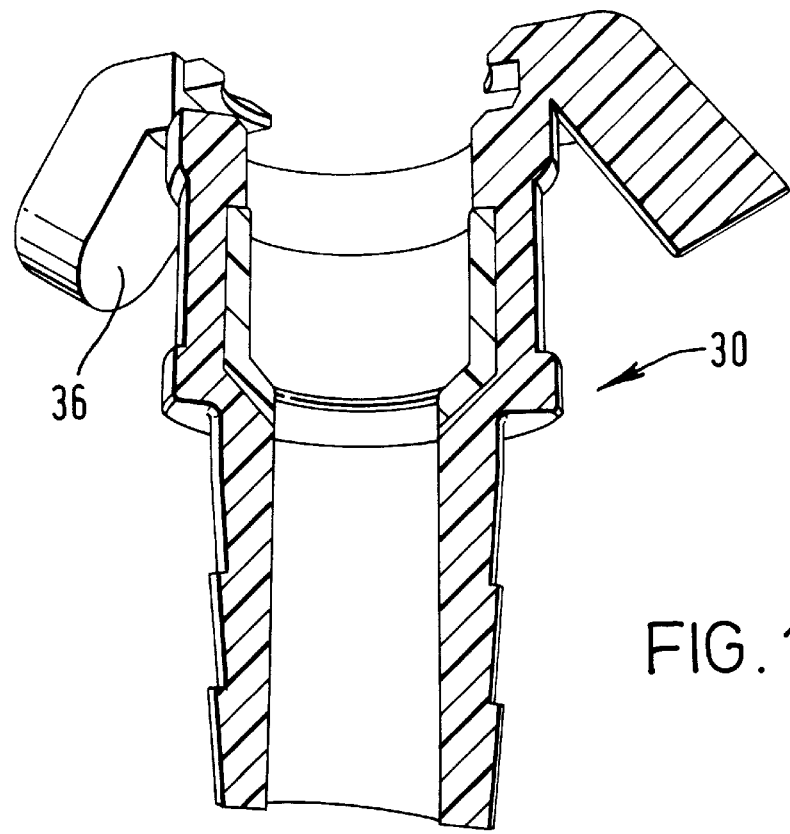
FIG. 1 is a perspective view of a female coupling part shown cross-sectioned in two axial planes at about 160 degrees to each other, and seen from slightly below.

The illustrated coupling 10 includes a male coupling part 20 and a female coupling part 30. The two coupling parts are generally tubular in form, and both may be made of synthetic plastics material. The male coupling part 20, seen in FIG. 4, is essentially a hollow tube open at both ends having a peripheral rib 22 below which is located a smooth cylindrical portion 21 whose lower outer edge at 23 is chamfered for example at 45°. Located just above the peripheral rib 22 is a second peripheral rib 24. The space 25 between ribs 22 and 24 receives a pair of tabs (which will be later described) which form part of the female coupling element 30. As seen in FIG. 4, the upper part of the tube 20 has internal stepped portions 28 designed to grip the internal surface of a conventional plastics tube such as is employed, for example, with catheters or urine drainage bags. Of course, instead of stepped portions on the outside of the male coupling part, a corrugated or stepped formation may be provided on the inner surface to facilitate attachment of tubes.

Figure 2:
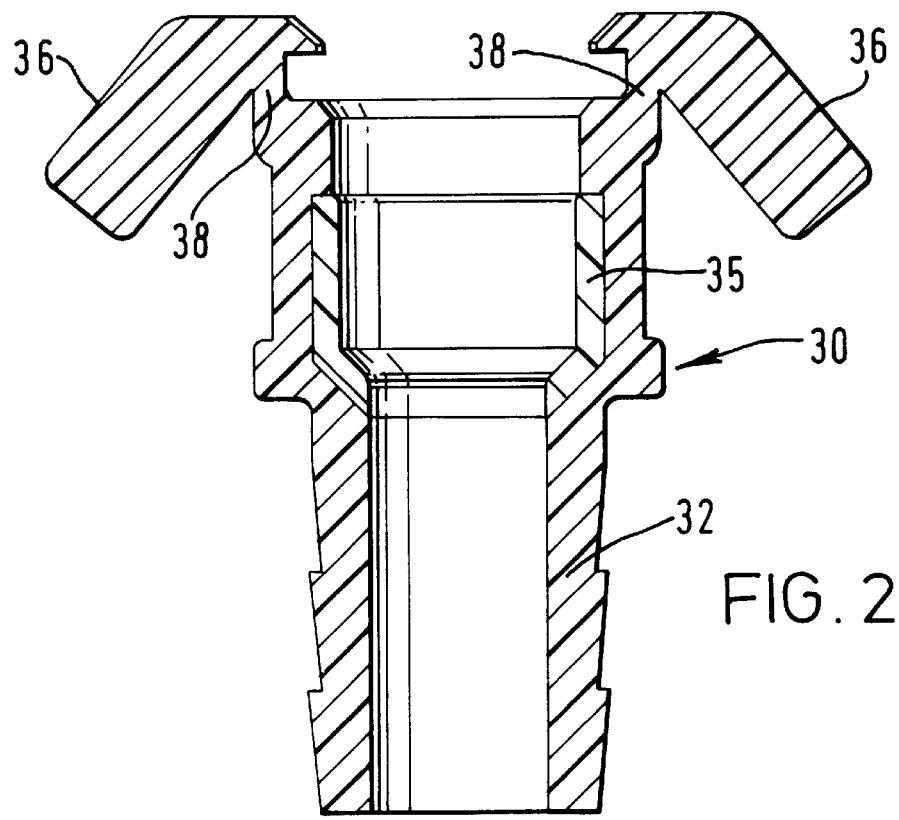
FIG. 2 is an axial cross-section of the female part shown in FIG. 1.

The female coupling part 30 is shown in FIGS. 2 and 4 and comprises a tubular shell portion 32, and an enlarged free end portion 34, these two portions being joined by an internal surface sloped at approximately 45°. Within the enlarged end portion 34 there is a recess defined by walls 31 and this recess contains a cushioning and sealing portion 35 of the female coupling part. At the upper end of the female coupling part as seen in FIG. 4 there are a pair of tabs 36 joined by respective integral plastics hinges 38 to the free (upper) end of the enlarged end portion 34. By applying pressure to these tabs in the direction of the arrows A the tabs 36 pivot relative to the female coupling part 30 and their hook portions 37 are hence shifted approximately radially outwardly, so moving clear of the rib 22 and releasing the male coupling part 20 which can then be axially withdrawn, thus separating the coupling parts.

An important advantage of the present invention is that the female coupling part can be inexpensively made by a "two-shot" moulding process whereby in the first stage the female part 30 is moulded and in the second stage the cushioning and sealing portion 35 thereof is moulded within the recess 31. The female coupling part 30 is moulded from a relatively rigid thermoplastic elastomer in the aforesaid first stage; and in the aforesaid second stage, a relatively soft thermoplastic elastomer is moulded to form the cushioning and sealing portion 35. As best seen in FIG. 4, the spigot end 21 of the male coupling part extends into contact with the internal surface of the cushioning and sealing portion 35. In this way an effective seal between the male and female coupling parts is achieved, together with a facility for rapid release and separation. In contrast to earlier designs of medical tube couplings, there are no loose parts which may easily get lost. The outside diameter of the spigot portion 21 of the male coupling part and the inside diameter of the cushioning and sealing portion 35 may be chosen so that there is an interference fit between these portions when the coupling is in its assembled condition. The extent of the interference fit in an optimum case will depend on the materials used; the spigot 21 may for example be oversize by a few thousandths of an inch (a few hundredths of a millimeter). The female coupling part (excluding the cushioning and sealing portion) may be moulded from a relatively rigid thermoplastic elastomer known as "HYTREL" which may be obtained from the Du Pont Company. Other materials can alternatively be used.

Modifications may be made without departing from the invention. For example, the recess which receives the cushioning and sealing portion may be of a different shape to that illustrated. There may be three tabs 36 at 120° spaced around the axis of the female coupling part, or 4 tabs at 90°, instead of the two illustrated diametrically opposed tabs.

We claim:

1. A tube coupling comprising:

a male tubular coupling member having an end portion, said end portion having a predetermined length and a consistent outer circumference, said end portion also including a free end and a radially outward extending peripheral rib proximate to said free end, a hollow female tubular coupling member having an open passageway for receiving a portion of said male tubular coupling member therein, said female member having a plastic outer shell, said shell having an inner surface with an annular recess therein, said female member having integral fastening hooks for detachably capturing said peripheral rib, each of said hooks having a corresponding radially outwardly extending tab portion, each of said hooks being resiliently expandable outwardly to permit said female member to receive said free end of said male member and resiliently contractible to capture said rib, said hooks being expandable outwardly to detach said captured rib upon application of pressure to said corresponding tab portions, said male and female members being coupled together when said rib is captured by said fastening hooks, a soft annular cushioning member within said recess, said cushioning member including an untapered tubular portion and an angled tapering portion extending therefrom, said untapered tubular portion being conformable to said outer circumference along the entire length of said end portion of said male member, said angled tapering portion tapering said open passageway inwardly, said angled tapering portion sealingly abutting said free end when said male and female parts are coupled together so as to reduce the possibility of leakage.

2. The tube coupling of claim 1 wherein said cushioning member is plastic.

3. The tube coupling of claim 1 wherein said cushioning member is a thermoplastic elastomeric material.

\* \* \* \* \*